(12) United States Patent
Schaefer (10) Patent No.: US 10,489,647 B2
(45) Date of Patent: Nov. 26, 2019

(54) METHOD FOR COMPUTING A UNIQUE IDENTIFIER FOR A GEMSTONE HAVING FACETS

(71) Applicant: INEXTO SA, Lausanne (CH)

(72) Inventor: Nicolas Schaefer, Orbe (CH)

(73) Assignee: Inexto S.A., Lausanne (CH)

( * ) Notice: Subject to any disclaimer, the term of this patent is extended or adjusted under 35 U.S.C. 154(b) by 73 days.

(21) Appl. No.: 15/950,278

(22) Filed: Apr. 11, 2018

(65) Prior Publication Data

US 2018/0300546 A1 Oct. 18, 2018

(30) Foreign Application Priority Data

Apr. 14, 2017 (EP) ...................................... 7166692

(51) Int. Cl.
*G06K 9/00* (2006.01)
*G01N 21/87* (2006.01)

(52) U.S. Cl.
CPC ......... *G06K 9/00577* (2013.01); *G01N 21/87* (2013.01)

(58) Field of Classification Search
CPC .......................... G06K 9/00577; G01N 21/87
See application file for complete search history.

(56) References Cited

U.S. PATENT DOCUMENTS

| | | | |
|---|---|---|---|
| 3,947,120 A | 3/1976 | Bar-Issac | |
| 5,124,935 A | 6/1992 | Wallner | |
| 5,983,238 A | 11/1999 | Becker | |
| 6,239,867 B1 | 5/2001 | Aggarwal | |
| 6,980,283 B1 | 12/2005 | Aggarwal | |
| 8,270,719 B2 | 9/2012 | Ellawand | |
| 8,744,188 B2 | 6/2014 | Ellawand | |
| 9,151,717 B2 | 10/2015 | Schnitzer | |
| 9,152,862 B2 | 10/2015 | Ross | |
| 9,188,542 B2 | 11/2015 | Smith | |
| 9,519,961 B2 | 12/2016 | Schnitzer | |

(Continued)

FOREIGN PATENT DOCUMENTS

| | | |
|---|---|---|
| EP | 0042361 | 12/1981 |
| WO | WO 99/61890 | 12/1999 |

(Continued)

OTHER PUBLICATIONS

European Search Report for Application No. 17166692.8 dated Oct. 9, 2017 (6 pages).

*Primary Examiner* — Bobbak Safaipour
(74) *Attorney, Agent, or Firm* — Mueting, Raasch & Gebhardt, P.A.

(57) ABSTRACT

The invention relates to method for computing a unique identifier for a gemstone, including acquiring a 2D digital master image of the gemstone, where an image of a reference mark on the gemstone defines a master image referential; matching a virtual selection mask with the master image according to a predefined position and orientation with respect to the master image referential; defining, in the master image, a plurality of distinct selected zones corresponding to the location of selection zones of the matched mask; detecting, in each of the plurality of distinct selected zones, the presence or not of at least one facet edge portion image; defining a location of the detected facet edge portion images in the master image; and computing a unique identifier based on the defined locations of the detected facet edge portion images.

15 Claims, 5 Drawing Sheets

(56) References Cited

U.S. PATENT DOCUMENTS

| | | | |
|---|---|---|---|
| 2006/0267975 A1* | 11/2006 | Moses | G01N 21/87 |
| | | | 345/419 |
| 2012/0007971 A1 | 1/2012 | Schnitzer | |
| 2015/0371087 A1 | 12/2015 | Ross | |
| 2016/0004926 A1 | 1/2016 | Kerner | |
| 2016/0041106 A1 | 2/2016 | Smith | |
| 2016/0203495 A1* | 7/2016 | Koh | G06Q 10/06 |
| | | | 705/317 |
| 2016/0232432 A1 | 8/2016 | Regev | |

FOREIGN PATENT DOCUMENTS

| | | |
|---|---|---|
| WO | WO 2006/117406 | 11/2006 |
| WO | WO 2010/010375 | 1/2010 |
| WO | WO 2010/103526 | 9/2010 |
| WO | WO 2014/036460 | 3/2014 |
| WO | WO 2016/054996 | 4/2016 |
| WO | WO 2016/127064 | 8/2016 |
| WO | WO 2016/185472 | 11/2016 |

\* cited by examiner

METHOD FOR COMPUTING A UNIQUE IDENTIFIER FOR A GEMSTONE HAVING FACETS

PRIORITY

This application claims the benefit of priority under 35 U.S.C. § 119(a) of European Application No. 17166692.8 filed Apr. 14, 2017, the disclosure of which is incorporated by reference herein in its entirety.

TECHNICAL FIELD

The invention relates to the field of gemstone identification.

BACKGROUND ART

Gemstones, whether precious or semi-precious, may have a high monetary value, which makes them prone to robbery or falsification. Therefore, there are many advantages in being able to identify gemstones in a unique way. It is known to identify gemstones through the use of an identification code. Such code can be marked on the gemstone. However, markings can be easily erased or replaced and thus are not secure enough. Document US-2016/0232432 discloses systems and methods for identification of gemstones. The gemstones can be imaged and image analysis can quantify one or more external and/or internal characteristics of the gemstone. The quantification of the one or more external and/or internal characteristics of the gemstone can be compared to a previous characterization to positively identify the gemstone. Proposed methods include line and shape matching. Such methods can involve heavy computation and may necessitate the provision of several images of the gemstone under different viewing angles. Therefore, such methods may be inadequate to identify uniquely a great amount of gemstones within reasonable computing time and computing power. Typically, such methods would be inadequate for cases where the method is to be applied to over one million gemstones per year, or even ten million gemstones per year.

Therefore, the invention has the object of providing a method for computing a unique identifier for a gemstone with limited computing time and limited computing power, while providing a reliable unique identifier.

Indeed, for a given gemstone the unique identifier may be computed a first time, to obtain an original identifier. Such original identifier can be stored in an original identifiers database, for example with other items of information relating to this gemstone (weight, color, clarity, cut, origin, producer, current owner, etc. . . . ).

At later point in time, in order to recognize and identify the same gemstone, a new computation using the same method for computing a unique identifier is used to compute a retrieved identifier. This retrieved identifier can be compared to the original identifiers in the original identifiers database to find a matching original identifier. If a matching original identifier is found, then the gemstone is positively identified and the associated items of information for that gemstone can be retrieved.

Therefore, the method for computing a unique identifier must have a high repeatability.

SUMMARY

The invention relates to a method for computing a unique identifier for a gemstone having facets separated by facet edges, comprising:

acquiring a 2D digital master image of the gemstone with a digital photographic imaging device, the digital image comprising a 2D array of pixels having a pixel value, where an image of a reference mark on the gemstone is included in the master image at a reference location with a reference orientation, thus defining a master image referential based on the reference location and on the reference orientation;

using a predefined virtual selection mask wherein the virtual selection mask comprises a series of distinct selection zones, and matching the virtual selection mask with the master image according to a predefined virtual selection mask position and predefined virtual selection mask orientation with respect to the master image referential;

defining, in the master image, a plurality of distinct selected zones corresponding to the location of the selection zones of the matched mask;

detecting, in each of the plurality of distinct selected zones of the master image, the presence or not of at least one facet edge portion image;

in the presence of at least one detected facet edge portion image, defining a location of the detected facet edge portion images in the master image;

computing a unique identifier based on the defined locations of the detected facet edge portion images.

According to other optional features of the invention, which can be included alone or in combination:

The unique identifier may be computed based on a computed origin distance for the detected facet edge portion images, where the origin distance for a detected facet edge portion image is the distance between the defined location of the detected facet edge portion image and the reference location of the reference mark.

The method may further comprise:
  detecting, in each of the plurality of distinct selected zones of the master image, the presence or not of two distinct facet edge portion images;
  in the presence of two detected facet edge portion images in a same selected zone of the master image, defining a location of each of the two detected facet edge portion images in the master image and computing an inter-edge distance between the two defined locations of the detected facet edge portion images;
  computing the unique identifier based on the computed inter-edge distances.

The unique identifier may be computed based on the computed origin distances and on the computed inter-edge distances for the detected facet edge portion images.

A selection zone of the virtual selection mask may be defined by a selection path curve associated with an analysis window having an analysis area measured in pixels, a selected zone in the master image being the array of pixels of the master image which are covered by the analysis window when the analysis window of a corresponding selection zone of the matched virtual selection mask is circulated along the associated selection path curve.

The series of selection zones of the virtual selection mask may be defined by at least one series of distinct selection path curves.

The series of selection zones of the virtual selection mask may be defined by at least one series of distinct parallel selection path curves.

The series of selection zones of the virtual selection mask may be defined by at least one series of distinct parallel straight selection path lines.

A facet edge portion image may be detected by:
  computing a window value for successive window positions of the analysis window along the selection path curve of a selection zone, where the window value for a given window position along the selection path curve is computed based on the pixel values of pixels of the master image which are covered by the analysis window at said given position;
  monitoring the variation of the window value when the analysis window is circulated along the selection path curve;
  detecting a facet edge portion image based on the variation of the window value.

A facet edge portion image may be detected when the variation of the window value shifts with respect to a threshold value.

The method may include a prior step of placing the gemstone with respect to the imaging device in a position and orientation so that the image of the reference mark on the gemstone is included in the master image at a predefined reference position.

The method may include a prior step of placing the gemstone with respect to the imaging device in a position and orientation so that the image of the reference mark on the gemstone is included in the master image with a predefined orientation.

The reference mark may be a preexisting known reference mark on the gemstone.

The master image may be acquired under specified illumination conditions.

BRIEF DESCRIPTION OF THE DRAWINGS

The method of the present invention will be further described in detail below with reference to the accompanying drawings showing preferred embodiments of the apparatus of the invention.

In the figures.

DETAILED DESCRIPTION OF SOME EMBODIMENTS

Figure 1:
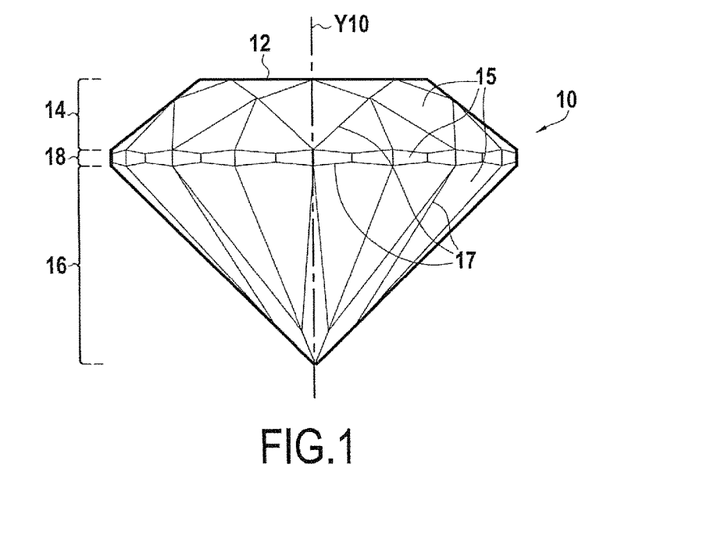
FIG. 1 represents schematically an example of a cut gemstone having facets.

FIG. 1 shows a gemstone for which the method according to the invention can be implemented. In this example, the gemstone can be a diamond. The gemstone 10 is a cut gemstone, meaning that planar facets have been created, two facets of the gemstone being separated by a facet edge. In the shown example, the cut is a classical round cut. However, the invention is applicable to any type of gemstone cut. In the shown example, the gemstone exhibits a top table facet 12. The top part of the gemstone is conventionally called the crown 14 while the bottom part of the gemstone is conventionally called pavilion 16. The terms top and bottom used herein are used only in a relative sense, in relation to the orientation of the gemstone 10 as shown on FIG. 1. These terms should not be interpreted as a limitation to the invention. This example of a gemstone thus exhibits an axis of symmetry Y10 which is perpendicular to the top table facet 12. The perimeter which extends between the crown 14 and the pavilion 16 is called the girdle 18. The peripheral extension of the girdle 18 extends in a plane perpendicular to the axis of symmetry Y10 of the gemstone 10. The crown 14, the pavilion 16 and the girdle 18 each comprise multiple facets 15 separated by facet edges 17. In this example, it will be considered that the facets of the girdle 18 extend each in a plane which is parallel to the axis of symmetry Y10 of the gemstone.

Figure 2:
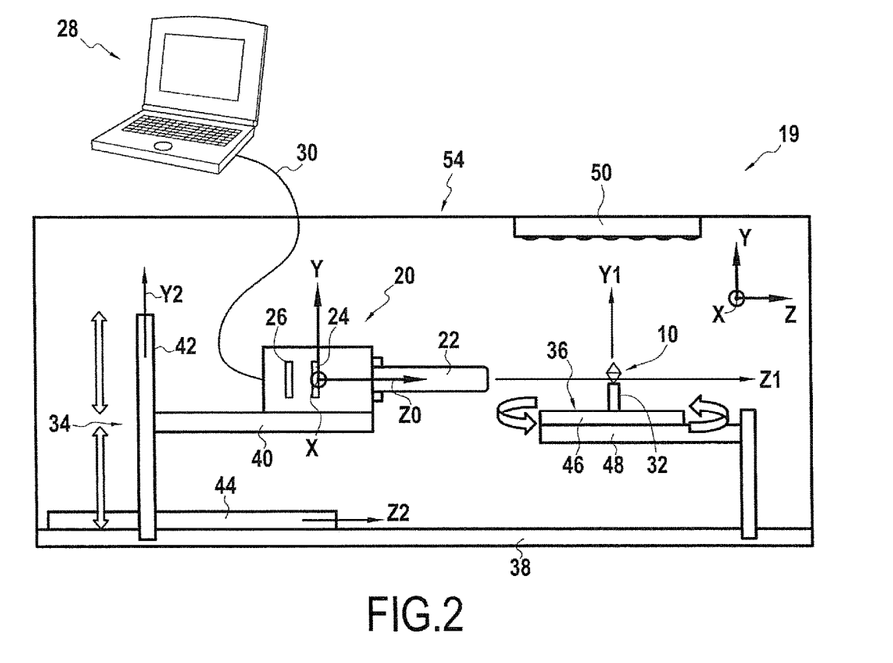
FIG. 2 represents schematically an embodiment of some components of an imaging system for carrying out the invention.

The invention relates to a method for computing a unique identifier for a gemstone having facets, for example for a gemstone as depicted on FIG. 1. The method for computing the unique identifier involves acquiring a 2D digital master image of the gemstone with a digital photographic imaging device. On FIG. 2 is shown one example of an imaging system 19 which can be used for acquiring such a master image.

The imaging system 19 is based on an imaging device 20 capable of acquiring a 2D image of an object and of delivering a digital photographic image of said object, typically in this case of a gemstone. Typically, the imaging device 20 can be a digital camera, either a video camera or a stills camera. The imaging device 20 typically comprises a lens 22, a photoelectric array sensor 24 and electronics 26 for delivering a digital image based on an optical image formed by the lens 22 on the photoelectric array sensor 24. The photoelectric array sensor 24 is conventionally made of a two dimensional array of photoelectric elements and it conventionally extends in a plane which, in this example, extends along two perpendicular directions X and Y. The photoelectric array sensor 24 can for example be of the CCD type or of the CMOS type. The lens 22 has an optical axis which extends along an axis Z0 which is parallel to a direction Z perpendicular to both directions X and Y. Preferably the lens 22 is a telecentric lens. The use of a telecentric lens also can help in reducing the difficulty in evaluating distances on the object through an analysis of the image of the object. However, it is not compulsory, especially in view of the fact that the master image is not used for making an absolute measurement, but rather for a relative measurement.

The electronics 26 of the imaging device 20 can store the digital image that they deliver under electronic format in a digital data storage device, for example either to a removable memory card, and/or to a RAM of the electronics. The digital image may be sent, immediately or upon request, to a computer system, for example a computer 28, for example through an external communication port of the imaging device. The external communication port can be connected to such a computer system, for example the computer 28, by a communication link 30 which can be a wired communication link, for example a USB cable link or an Ethernet cable link, or a wireless communication link, for example a Bluetooth or Wi-Fi communication link; or a wireless GSM, GSM/EDGE, CDMA2000, TD-SCDMA, UMTS, LTE, etc. . . . mobile communication link. The computer 28 is merely an example of a computing device or computing system which can be used to implement the invention. More examples will be given at the end of this specification. The communication link may include the Internet.

As the imaging system 19 is designed to acquire images of gemstone 10, it is preferably equipped with a gemstone holder 32. The imaging system 19 is configured to allow the positioning of the gemstone 10 in a desired position and a desired orientation in front of the imaging device 20, along the optical axis Z0. Therefore, the imaging system 19 preferably comprises a positioning system for adjusting the relative position and orientation of the gemstone 10 and of the imaging device 20.

In the depicted arrangement, the positioning system comprises an imaging device positioning system 34 and an object holder positioning system 36, for positioning respectively the imaging device 20 and the object holder 32 with respect to a chassis 38 of the imaging system 19. However, only one of the two systems may be provided, possibly with more adjustment possibilities. In the shown embodiment, the chassis 38 may take the form of a base plate extending in a plane parallel to the X and Z directions.

The imaging system 19 shown in FIG. 2 is designed more specifically for acquiring 2D images of the gemstone as shown above, from the side, i.e. from a direction perpendicular to the axis of symmetry Y10 of the gemstone. This imaging system 19 is thus adapted for acquiring images of gemstones which may be used in a first example of the method which will be described in relation to FIGS. 3, 4 and 5. In the shown example, the positioning system allows for adjustment according to only two directions in translation, in this example directions Y and Z, and for adjustment in rotation according to only one axis, in this example around an axis Y1 parallel to the direction Y of the plane of the photoelectric array sensor 24. Indeed, in this embodiment, the object holder 32 occupies a fixed position along the direction X with respect to the imaging device 20.

For example, the imaging device positioning system 34 is able to displace the imaging device 20 along the two perpendicular directions Y and Z. For example, the imaging device positioning system 34 comprises a platform 40 on which the imaging device 20 is firmly secured. The platform 40 is mounted on a column 42 oriented along an axis Y2 parallel to the direction Y, with the possibility for the platform 42 to be displaced along the axis Y2 with respect to the column 42, for example through a slide connection. The column 42 is itself mounted on a rail 44 which extends along axis Z2, parallel to direction Z, and which is fixed with respect to the chassis 38, with the possibility for the column 42, and thus also for the platform 40, to be displaced along the Z direction. Also as a matter of example, the object holder positioning system 36 comprises the turntable 46 which is mounted on a support 48, which can be fixed with respect to the chassis 38, the turntable being rotatable along an axis Y1 parallel to the direction Y. The object holder 32 is mounted on the turntable 46. In the shown example, the object holder 32 comprises a tube having an axis coincident with the rotation axis Y1 of the turntable 46. The object holder 32 is configured to hold the gemstone 10 of FIG. 1 with its axis of symmetry Y10 coincident with the axis Y1 of rotation of the turntable.

Preferably, one or more of the relative displacements allowed by the positioning system is motor driven for example with the provision of an electric motor. Preferably, one or more of the relative displacements allowed by the positioning system is controlled through the computer 28, which may control the corresponding electric motor. As will be explained more in detail below, the positioning system allows for a user of the imaging system 19 to manually or automatically cause a relative displacement of the gemstone 10 with respect to the imaging device 20 such that a desired relative position is achieved.

The imaging system 19 preferably comprises a lighting device 50 for lighting the gemstone 10 according to specified illumination conditions. The specified illumination conditions will vary according to the geometry of the gemstone and according to the part of the gemstone for which an image is to be acquired. The lighting device 50 will thus be adapted so as to be either a punctual source of light or an extended source of light, a unidirectional source of light or multi-directional, i.e. diffuse, source of light, a monochromatic source of light or multi-chromatic source of the light, etc. . . . . The lighting device 50 may combine several light sources having different sets of such features. Also, the lighting device 50 will be positioned and oriented with respect to the gemstone 10 and with respect to the imaging device 20 in order to achieve the right contrast in the digital image acquired with the imaging device 20. The lighting device 50 may be positioned and oriented such that the light acquired by the imaging device 20 is light which is reflected, and/or, in the case of transparent or at least translucent gemstones, refracted or transmitted by the gemstone. The choice of the proper illumination conditions is within the skills of the man in the art, based on his experience and with limited testing, knowing that in most cases, several illumination conditions may be suitable for the method according to the invention.

In the shown example, where it is desired to acquire the digital image of the girdle 18 of the gemstone 10 from the side of the gemstone, the lighting device 50 may comprise a series of LEDs which are oriented to illuminate the gemstone from the top, that is to illuminate the gemstone with light directed along the general direction perpendicular to the top table facet 12 of the gemstone, from above the top table facet, i.e. from a direction opposite from the pavilion 14. The LEDs are arranged so as to form an extended light source compared to the size of the gemstone. The light source here extends in a plane parallel to direction X and perpendicular to the axis of symmetry Y1 of the gemstone. Preferably, the LEDs are arranged to form a source of light which is arranged symmetrically with respect to the axis of symmetry Y1 of the gemstone. The LEDs of the lighting device 50, when combined, form a source of diffuse light. In the case of a diamond gemstone, the LEDs may emit blue light, having a wavelength comprised within 380 to 500 nanometers. Such blue light has been found to be favorable for better contrast in the master image, at least for the configuration shown in FIG. 2 when the zone of interest on the gemstone is the girdle 18.

In the shown example, the imaging device 20, the object holder 32 and the lighting device 50 of the imaging system 19 are preferably encased in a casing 54 for shielding the object from other sources of light than the light provided by lighting device 50. Preferably, the imaging device positioning system 34 and the object holder positioning system 36 are also comprised within the casing 54, the casing 54 being for example fixed to the chassis 38 of the imaging system 54. The casing 54 may comprise peripheral walls made of opaque material. One or more of the peripheral walls of the casing 54 may be removable and/or may comprise an access door for providing access to the imaging device 20 and to the object holder 32. The casing 54 may be removable as a whole from the chassis 38.

One step of the method according to the invention includes acquiring 2D digital master image of the gemstone 10 with a digital photographic imaging device such as the imaging device 20 described above. The master image comprises a 2D array of pixels having a pixel value, but it can also comprise additional data. The image acquisition is made such that one pixel of the image corresponds to one location on the gemstone in the field of view. It is understood that the master image MI is acquired with settings according to which a zone of interest on the gemstone is in focus. Thus, the lens 22 produces an optical image of the zone of interest of the gemstone on the photoelectric array sensor 24, the optical image and the zone of interest being conjugate through the lens 22.

Figure 3:
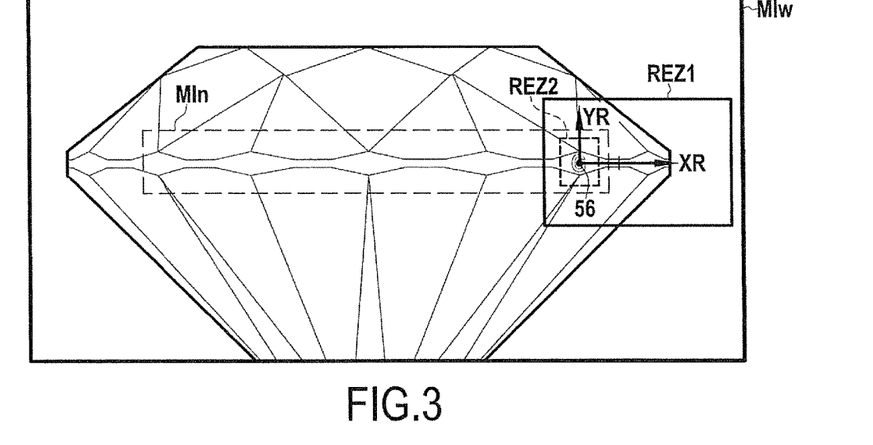
FIG. 3 is an example of a graphical representation of a digital image of the cut gemstone of FIG. 1 which can be used as a master image in the method according to the invention.

The master image MI can be an image of a field of view which is only partly occupied by the gemstone 10 as shown by the wide master image MIw of FIG. 3. In this particular case, the field of view is only partly occupied by the gemstone and the field of view only covers parts of the gemstone. In that case, some of the pixels of the master image correspond to a location on the gemstone 10 while other pixels correspond to a location in the background. The master image can be an image of a field of view which is fully occupied by the gemstone 10 as a shown by the narrow master image MIn. In the latter case, all pixels of the image correspond to a location on the gemstone. In both cases, whether the master image is a wide master image MIw or a narrow master image MIn, it may be the full image acquired by the imaging device 20 or it may be a cropped image derived from the full image acquired by the imaging device 20.

The size of the master image in terms of number of pixels can be anywhere between for example 200,000 pixels to 50 million pixels or more.

With the imaging system 19 described in relation to FIG. 2, the array of photoelectric elements of the photoelectric array sensor 24 are preferably arranged in rows and columns, rows extending along the direction X and columns extending along the direction Y.

The pixel value of each pixel can be any value representative of the light intensity emitted by the corresponding location in the field of view of the imaging device 20. In a typical case where the imaging device delivers an RGB (red, green, blue) image, the pixel value may be the value of any one of the three red, green or blue channels of the RGB image for that pixel, or a combination of those values. Typically, the pixel value in the master digital image can be a greyscale value. The pixel value may be an 8-bit value ranging from 0 to 255, 0 corresponding to no light intensity and 255 corresponding to maximum light intensity. The master image is a digital image, thus a two dimensional array of numbers corresponding to the pixel values. The master image is stored in electronic format, transiently or permanently, in a digital data storage device. The master image may be electronically duplicated, transferred, etc. . . . . .

In the method according to the invention, the gemstone 10 is positioned with respect to the imaging device 20 for the acquisition of the master image so that an image of a reference mark 56 on the gemstone 10 is included in the master image at a reference location with a reference orientation, thus defining a master image referential based on the reference location with a reference orientation.

The reference mark 56 can be any mark on the gemstone 10, including on a surface of the gemstone and/or in the inside of the gemstone. Preferably, the reference mark is a preexisting known reference mark on the gemstone.

In some instances, the reference mark 56 can be a natural mark originally present on the gemstone before the gemstone being cut, including for example an inclusion in the gemstone. However the reference mark 56 is preferably a man-made mark on the gemstone. The reference mark 56 can be a mark resulting from the cut of the gemstone.

However the reference mark 56 is preferably a dedicated reference mark, the shape of which is chosen in view of being reliably recognized and analyzed in an imaging analysis process, for example through pattern matching, to retrieve therefrom a position of the mark and an orientation of the mark.

Examples of pattern matching technologies which can be used for detecting the reference mark 56, and for retrieving its position and orientation in the master image, include commercially available technologies such as PatMax® technology from COGNEX Corporation, 1 Vision Drive, Natick, Mass., USA. Pattern matching is for example performed by the computing system, for example by the computer 28.

The reference mark 56 is thus preferably a mark which does not have an axis of symmetry along the X and Y directions, preferably a mark which is devoid of any axis of symmetry. It can be a geometrical shape, for example a non-isosceles triangle. It can be a numerical or alphabetical character. For example the characters G, R, J can be used as a reference mark. The size of the mark is preferably small in comparison to the size of a facet of the gemstone. Typically, the size of the reference mark 56 can be such that it is contained within a square of less than 0.1 millimeter by 0.1 millimeter, preferably one less than 0.01 millimeter by 0.01 millimeter. In the master image, the image of the reference mark is preferably of a size larger than 30 pixels by 30 pixels, more preferably larger than 50 pixels by 50 pixels, in order to provide a precise position and orientation of the mark.

The reference mark 56 can be for example printed or engraved on the gemstone 10. The reference mark is preferably affixed on or near a zone of interest of the gemstone which is to be used for computing the unique identifier. Indeed, not all of the gemstone needs to be used to create a reliable unique identifier thanks to the method according to the invention. For example in a first example of the method which is to be described in relation to FIGS. 3, 4, and 5, the zone of interest corresponds to a part of the girdle 18 of the gemstone. In a second example of the method which is to be described in relation to FIGS. 6 to 10, the reference mark 56 may be affixed to the top table facet 12 of the gemstone or affixed to the gemstone so that it can be viewed through the gemstone 10 and through the top table facet 12. In the latter case, the zone of interest is the crown of 14 of the gemstone.

In the master image, the location of the image of the reference mark is defined as the reference location and the orientation of the reference mark is defined as the reference orientation.

In some variants of the invention, the reference position and/or orientation of the reference mark 56 is/are not predefined, and the image of the reference mark 56 can thus be anywhere and/or oriented anyhow in the mater image. In such a case, the reference position and/or orientation of the reference mark 56 are simply the position and of the reference in the acquired master image, without any constraint.

Figure 4:
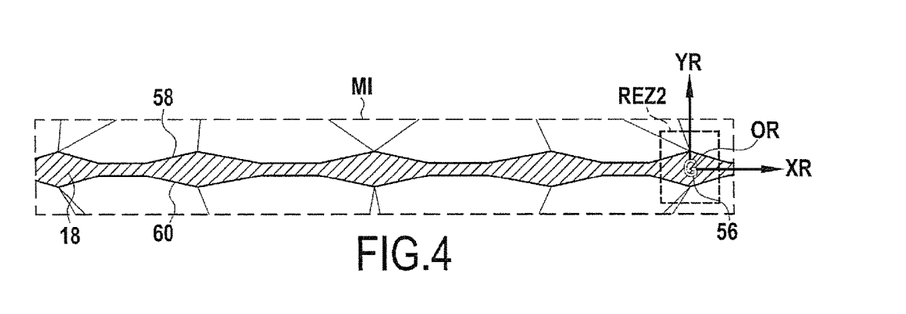
FIG. 4 is an example of a crop of the image of the cut gemstone of FIG. 3 which can be used as a master image in the method according to the invention.
Figure 5:
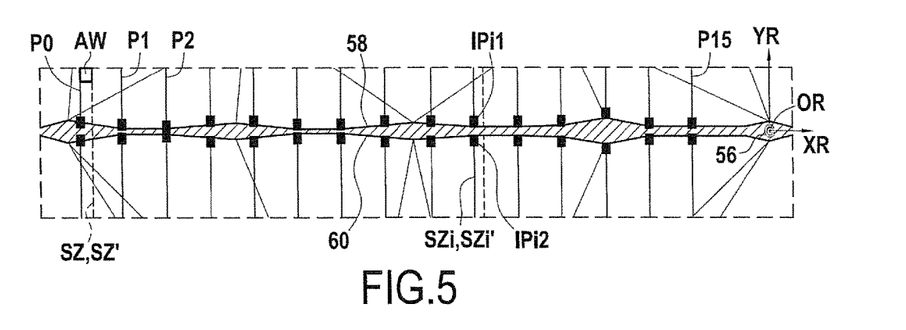
FIG. 5 represents schematically the matching of a virtual selection mask with the master image of FIG. 4.

To the contrary, in some variants of the invention, including the first example illustrated at FIGS. 3, 4 and 5, the reference location of the reference mark 56 is expected to be within a reference expectation zone REZ1, REZ2 of the master image or may be expected to be at an expected reference location in the master image. A reference expectation zone REZ1, REZ2 of the master image is a portion of the master image which is smaller than the master image and which at predefined fixed location in the master image. Typically, a reference expectation zone is less than half of the master image in pixel size, preferably less than one quarter of the image of the master image in pixel size. Typically, a reference expectation zone is more than 100 pixels by 100 pixels of the master image in pixel size.

Thus, the method may include a prior step of placing the gemstone 10 with respect to the imaging device 20 in a position and orientation so that the image of the reference mark 56 on the gemstone is included in the master image at a predefined reference position, possibly also with a reference orientation, or at least within a predefined reference expectation zone, possibly within a reference orientation range.

In the first example where the zone of interest is the girdle 18, it is for example expected that the reference mark 56 is located in the right part of the master image. Two examples of a reference expectation zone are shown schematically on FIG. 3. One relatively large reference expectation zone REZ1 may be used for example in conjunction with wide master image MIw and where a relatively small reference expectation zone REZ2 may be used in conjunction with a narrow master image MIn. Of course, a relatively narrow reference expectation zone REZ2 can also be used with a wide master image MIw. In those cases, it is necessary to position the gemstone 10 in a certain range of expected positions or in a certain expected position with respect to the imaging device 20. In such a case, this positioning can be manual, partly manual, assisted, or fully automatic.

In the example of FIG. 2, the positioning of the gemstone 10 with respect to the imaging device 20 may first involve a manual step of positioning the gemstone 10 on the object holder 32. The design of the object holder 32 in itself may already achieve part of the positioning. For example in the example of FIG. 2, the object holder 32 is designed, for gemstones having a classic round cut, to place the gemstone 10 such that its axis of symmetry Y10 is placed coincident with axis Y1 of the object holder positioning system 36.

The imaging device positioning system 34 may then be used to adjust the position of the imaging device 20 according to axis Y2 and Z2 to position the gemstone 10 within the field of view of the imaging device. This positioning via the imaging device positioning system 34 may be done manually by an operator, possibly assisted via the simultaneous viewing of a live image required by the imaging device 20 which can be broadcast on a display of the computer 28. This positioning step may be fully automated for example through a computer program run on the computer, using image analysis of images provided by the imaging device and controlling actuators of the positioning system. The object holder positioning system 36 may be then used to position the reference mark 56 of the gemstone at the proper position in the field of view of the camera so that the image of the reference mark is located at an expected position or in an reference expectation zone of the image acquired by the imaging device. Similarly to the previous positioning step, this positioning step may be manual, partly manual, assisted, or fully automatic.

Therefore at this stage of the method, the method provides a master image MI, which is a digital image, in which an image of reference mark 56 on the gemstone is included in the master image MI at a reference location with a reference orientation, for example as shown in FIG. 4. For example, the reference location OR associated with the reference mark 56 can be the center pixel of a rectangular pixel window circumscribing the reference mark, or any other remarkable point of such rectangular pixel window, such as a corner. The reference orientation associated with a reference mark may be defined by two perpendicular axis XR, YR having a predefined orientation with respect to the mark as it is recognized in an image analysis which may for example of involve pattern matching. The reference location OR and the reference orientation XR, YR thus define the master image referential defined by the reference mark 56. The master image MI of FIG. 4 is a narrow master image of a portion of the girdle 18 of the gemstone in which the reference location OR of the reference mark is located at one extremity of the master image along the direction X of the master image. In the example of FIG. 4, the axis XR, YR which are derived from the reference mark 56 for defining the image referential, are parallel respectively to the directions X and Y of the photoelectric array sensor 24.

Figure 6:
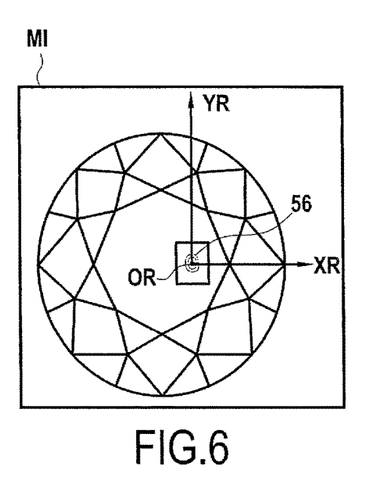
FIGS. 6 and 7 show a master image and its matching with a virtual selection mask for different master image of a different zone of interest on the gemstone.

In the example of FIG. 6, where the master image MI is essentially a top view along the axis of symmetry Y10 of the gemstone 10, the same situation arises where the reference mark 56 defines the master image referential whose orientation is parallel to the directions X and Y of the photoelectric array sensor. However, in the example of FIG. 9, which is similar to that of FIG. 6, the reference mark 56 defines a master image referential whose orientation is not parallel to the directions X and Y of the photoelectric array sensor 24, forming an angle A with the directions X and Y of the photoelectric array sensor 24.

In a preferred embodiment of the invention, the acquisition of the master image is performed by the imaging device 20, and the rest of the method is performed by the computer system, for example via computer 28.

According to an aspect of the method according to the invention, the method relies on the detection of those portions of the master image MI which correspond to the image of portions of facet edges 17 on the gemstone. However, in view of minimizing the computing power necessary for the method, the step of detecting the facet edge portion images within the master image MI uses image analysis techniques which are not applied to the full master image, but only to selected zones thereof.

The method according to the invention uses a predefined virtual selection mask. The virtual selection mask comprises a series of distinct selection zones SZ. The virtual selection mask will thus be used to select selected zones SZ' in the master image MI which will undergo image analysis for the detection of facet edge portion images. In other words the virtual selection mask serves for defining, in the master image, a plurality of distinct selected zones corresponding to the location of the selection zones mask.

The virtual selection mask is, or can be considered as, a set of values, which may be organized in a matrix, which may be stored electronically, and which is going to be used as coordinate values in the master image referential to identify which pixels in this master image referential will be retained for image analysis.

As an example, as shown on FIGS. 5, 7, 8 and 10, a selection zone of the virtual selection mask may be defined by a selection path curve P1, P2, P3, . . . , Pi, etc . . . , associated with an analysis window AW having an analysis area measured in pixels. The selection zone SZ is defined by the area which is covered by the analysis window AW when the analysis window is circulated along the selection path curve P1, P2, P3, . . . , Pi, . . . associated to that selection zone. As a result, a selected zone SZ' in the master image defines the array of pixels of the master image MI which are covered by the analysis window when the analysis window of a corresponding selection zone of the matched virtual selection mask is circulated along the associated selection path curve.

A selected zone SZ' is a sub-array of pixel values of the master image MI. A selected zone SZ' may be stored in electronic format, transiently or permanently, in a digital data storage device. The selected zone SZ' may be electronically duplicated, transferred, etc. . . . .

On FIGS. 5, 7, 8 and 10, only one selection zone SZ is shown, that corresponding with one selection path curve P0. Of course, the virtual selection mask which is shown on those figures comprises as many selection zones as there are selection path curves. On FIGS. 5, 7, 8 and 10, the virtual selection mask is represented in superposition with the corresponding master image MI, therefore the selection zones SZ in the virtual selection mask coincide with the selected zones SZ' in the master image MI.

In the example shown on the figures, the series of selection zones of the virtual selection mask is defined by at least one series of distinct parallel straight path lines, which typically correspond to a row of pixels.

In such a case, the virtual selection mask could be formulated as the following matrix of virtual pixels having a binary value:

...

[...]001000000[...]00000000010000000[...]00000000100[...]

[...]001000000[...]00000000010000000[...]00000000100[...]

[...]001000000[...]00000000010000000[...]00000000100[...]

[...]001000000[...]00000000010000000[...]00000000100[...]

[...]001000000[...]00000000010000000[...]00000000100[...]

[...]001000000[...]00000000010000000[...]00000000100[...]

...

where a path curve consists of a group of proximate virtual pixels having a certain binary value, here a column of proximate virtual pixels having a 1 value.

However, not only straight lines can be used. Any series of distinct curves can be used. Preferably, the series of selection zones of the virtual selection mask is defined by a series of distinct parallel selection path curves which do not intersect each other. Typically, a series of distinct selection path curves can be a series of parallel wavy lines, or a series of concentric geometrical figures such as concentric circles etc. etc. It can be noted that the series of selection zones of the virtual selection mask may defined by a two or more series of distinct parallel selection path curves, where the selection path curves of one series do not intersect each other, but where the selection path curves of a given series may intersect selection path curves of another series.

Typically, the selected zones in the master image can represent, in terms of number of pixels, between 1% and 50% of the master image, preferably between 10% and 25%.

In some embodiments, as in the shown examples, the selected zones defined by the virtual selection mask may be spread at regular intervals. In other embodiments, the selection zones may be spread at irregular intervals. In some embodiments, the selected zones may be grouped in only one zone of interest of the master image.

As explained above, the method for computing the unique identifier will be used in a first process to determine the original unique identifier and will be used again one or more additional times in view of further recognizing a gemstone previously identified through the method. Each time the unique identifier is computed with the method, in order to make sure that it is always the same identification points which are used for the computation, the method provides that the virtual selection mask used for the computation is matched with the master image. Matching the virtual selection mask with the master image means that the virtual selection mask is associated to the master image according to a predefined virtual selection mask position and predefined virtual selection mask orientation with respect to the master image referential when determining, with the selection zones of the virtual selection mask, which are the selected zones of the master image.

Figure 7:
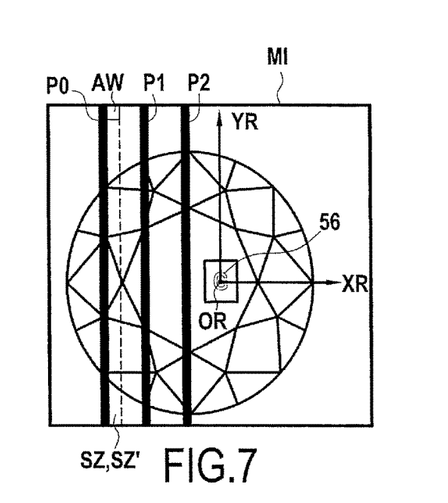
Figure 10:
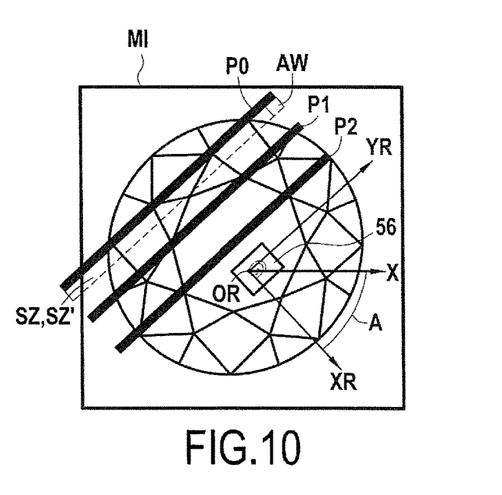

This step of matching the virtual selection mask with the master image is best understood in relation to FIG. 7 and FIG. 10. FIG. 7 and FIG. 10 may be two different master images of the same gemstone 10. Very evidently, it appears that the orientation of the gemstone 10 with respect to the imaging device 20 was not the same during the acquisition of the master images. However, thanks to the reference mark 56, it is possible in both master images to retrieve a master image referential (OR, XR, YR) for that master image, which is indicative of the orientation of the image of the gemstone in the master image. FIGS. 7 and 10 illustrate that the mask, as represented here by the selection path curves P0, P1, P2, . . . , Pi, . . . is in both cases brought to the same predefined virtual selection mask position and predefined virtual selection mask orientation with respect to the master image referential.

The step of matching the virtual selection mask with the master image may involve transforming either only one or both of the virtual selection mask and/or of the master image.

It may involve applying a rotation of the virtual selection mask and/or of the master image, according to a rotation angle A, and/or a translation of the virtual selection mask and/or of the master image according to the position of the reference mark.

For example, if the virtual selection mask is rotated in the matching process, a source virtual selection mask may be transformed to a matched virtual selection mask using a well-known rotation routine.

An example of rotation routine can be summarily described as follows, using pseudo-code:

```
MatchedMask=new int (rows,cols);
for (y=0; y<SourceMaskHeight; y++)
{
    for (x=0; x<SourceMaskWidth; x++)
    {
```

```
u = cos (A) * x+ sin (A) * y;
v = -sin (A) * x+ cos (A) * y;
MatchedMask [x, y] = SourceMask [u, v];
}
}
```

For example, in the case of 45° rotation of a source virtual selection mask as described above, the matched virtual selection mask could be formulated as the following matrix of virtual pixels having a binary value:

...

[...]001000000[...]00000000010000000 [...]00000000100[...]

[...]010000000[...]00000000100000000 [...]00000001000[...]

[...]100000000[...]00000001000000000 [...]00000010000[...]

[...]000000000[...]00000010000000000 [...]00000010000[...]

[...]000000000[...]00000100000000000 [...]00000100000[...]

[...]000000000[...]00001000000000000 [...]00001000000[...]

[...]000000000[...]00010000000000000 [...]00010000000[...]

...

A translation would of course result simply in the translation of the values in the matrix.

At least the source virtual selection mask may be of bigger size than the master image in terms of number of pixels, for example twice as big. The matched virtual selection mask may be cropped to the size of the master image in terms of pixels.

Once the selected zones in the master image are determined, the method provides for detecting, in each of the plurality of distinct selected zones of the master image, the presence or not of at least one facet edge portion image. Various known edge detection techniques can be used.

According to one possible technique, a facet edge portion image is detected by:
computing a window value for successive window positions AWj of the analysis window AW along the selection path curve of a selection zone SZ, where the window value for a given window position along the selection path curve is computed based on the pixel values of pixels of the master image which are covered by the analysis window at said given position;
monitoring the variation of the window value when the analysis window is circulated along the selection path curve;
detecting a facet edge portion image based on the variation of the window value.

Figure 11:
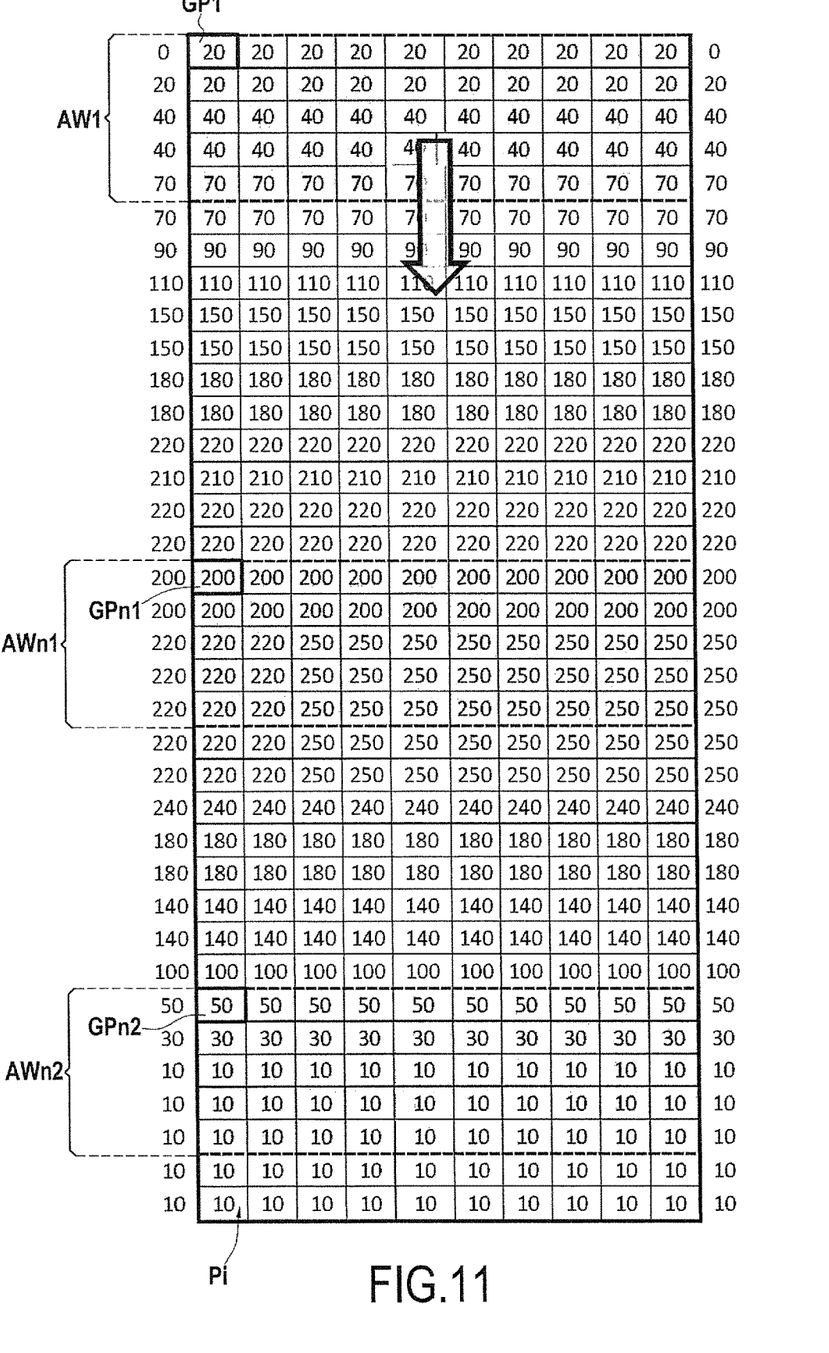
FIG. 11 illustrates a step of the method for detecting at least one facet edge portion image in the master image.

Such method is exemplified in FIG. 11. In FIG. 11 is shown a numerical representation of at least part of a selected zone SZ' in the master digital image. This representation shows a table where each cell includes a numerical value which is the pixel value of a corresponding pixel in the master image. A selected zone of the master digital image is represented which is defined by one column of pixel values Pi corresponding to one selection path curve of the virtual selection mask matched with the master image. In this example, an analysis window AW defines the selection zone SZ and thus the selected zone SZ'. In this example, the analysis window has a pixel area of 50 pixels, the analysis window having a width of 10 pixels along one direction XR in the master image referential and a height of 5 pixels along the perpendicular direction YR in the master image referential. However, other pixel areas could be chosen for the analysis window.

For the definition of the selected zone, the analysis window is circulated along the associated selection path curve. In this example, the top left pixel of the analysis window is arbitrarily chosen as the guiding pixel GP1, GPn1, . . . , GPn2, . . . of the analysis zone which will circulate along a selection path curve. The guiding pixel will, in the master image, follow the pixels of the master image which have the coordinates in the master image which correspond to coordinates of the virtual pixels forming the selection path curve in the matched virtual selection path.

The analysis window may thus occupy different window positions depending on which pixel of the selection path curve Pi is associated to the top left pixel of the analysis window. For each window position, the analysis window covers the pixel area, here 50 pixels, of the master image.

Therefore for each given window position it is possible to calculate a window value based on the pixel values of pixels of the master image which are covered by the analysis window at said given position. In the example of FIG. 11, three such analysis window positions AW1, . . . , AWn1, . . . , AWn2 (i.e. of the type AWj) are highlighted. The window value is for example a mathematical formula applied to those pixel values. The same mathematical formula is applied for each window position. For example the window value can be the arithmetic mean value of the pixel values of the pixels of the master image which are covered by the analysis window at said given position.

By monitoring the variation of the window value when the analysis window is circulated along the selection path curve, it is possible to detect the transition from for example a dark zone to a bright zone of the master image. This can therefore be interpreted as corresponding to the transition from the image of a dark facet on the gemstone to the image of a bright facet on the gemstone. For example, this detection may be based on detecting that the window value, from one window position to the next window position, shifts from one value below a high threshold value to a second value above the high threshold value. It is also possible to detect the transition from for example a bright zone to a dark zone of the master image This may be based on detecting that the window value, from one window position to the next window position, shifts from one value above a low threshold value to a second value below the low threshold value.

Therefore, when the monitoring of the variation of the window value detects such a shift in the window value with respect to a threshold value, it can be interpreted that the position of the analysis window corresponds to the location of the facet edge portion image. In the presence of at least one detected facet edge portion image, it is possible to define a location of the detected facet edge portion image in the master image. Indeed, in the above described technique, it is then possible to assign, as a defined location of this facet edge portion image, a value representative of the current position of the analysis window for which the shift was observed. This value representative the current position of the analysis window can be the coordinates of one pixel covered by the analysis window. It can be the coordinates of the guiding pixel, or of another pixel, for example the pixel corresponding to the center of the analysis window. This value is preferably expressed in the master image referential determined by the reference mark 56.

Monitoring the window values may include electronically storing the successive window values, at least transiently, in a digital data storage device of the computing device, for example a RAM (Random Access Memory). Detecting a shift in the window value with respect to a threshold value is typically performed by processor computation in the computing system. According to an example it may involve:
- computing, with the computer system, a first difference between a one window value and the threshold value;
- computing, with the computer system, a second difference between another window value, for example the one immediately following the said one window value, and the threshold value;
- verifying whether the first difference and the second difference are of the same mathematical sign or not.

The above-described edge detection technique which detects a facet edge portion image is particularly suitable for detecting and locating the image of an edge between a bright facet and the dark facet. Therefore the illumination conditions may be chosen, for the specific cut of the gemstone and for a given zone of interest on such gemstone, to provide such contrast between neighboring facets in the zone of interest. In the case where the zone of interest is the portion of the girdle 18, as described in relation to FIGS. 3, 4 and 5, the lighting device 50 which is described in relation to FIG. 2 provides, for the round cut shown in FIG. 1, a master image wherein the girdle facets, which are essentially parallel to the main lighting direction, appear very dark compared to the neighboring facets of the crown 14 and of the pavilion 16. Therefore, the above-described edge detection technique allows to detect and locate, within the master image, specific identification points associated with the detected facet portion images and which correspond, on the gemstone, to points on the edge of the girdle facets. The above-described edge detection technique thus returns the location within the master image of these identification points.

The location of the identification points are electronically stored, at least transiently, in a digital data storage device of the computing device, for example a RAM (Random Access Memory), or in any digital data storage device. Because these identification points have a location which is determined by the virtual selection mask, and because this virtual selection mask is matched to the master image through proper location and orientation with respect to the master image referential determined based on the reference mark 56, various successive implementations of the method, with the same gemstone and with the same or identical imaging system 19, will inevitably result in the detection of the same identification points.

According to an aspect of the invention, the method involves computing a unique identifier based on the defined locations of the detected facet edge portion images.

Various algorithms can be used to compute the unique identifier.

In some embodiments of the method, the unique identifier is computed based on a computed origin distance for the detected facet edge portion images. The origin distance for a detected facet edge portion image is the distance between the defined location of the detected facet edge portion image and the reference location of the reference mark.

This origin distance can be computed in the master image referential. In this referential, the origin OR of the master image referential may be assigned the coordinates (0, 0), while the coordinates of a given identification point IPij corresponding to the defined location of the detected facet edge portion image can be assigned the coordinates (Nij, Mij) which may be expressed in pixels. In such case, the origin distance DOij for that given identification point can be expressed by the formula valid for geometrical distance:

$$DOij = \sqrt{Nij^2 + Mij^2}$$

DOij may be rounded up to its integer part, to have an integer number.

Thus for example, the unique identifier for a given gemstone can be computed using various origin distance for a number of identification points detected for that gemstone.

In a given selected zone of the master image, there can be any number of identification points corresponding each to one detected facet edge portion image, for example 0, 1, 2, 3, 4, etc . . . , identification points in a given selected zone.

FIG. 5 illustrates, in an example, the various identification points which may thus be detected thanks to an edge detection technique, within the different selected zones of the image according to the virtual selection mask. In this example, it is seen that the master image comprises only the facets of the girdle 18 as dark facets compared to neighboring bright facets. Also, the selected zones of the master image which are defined by the virtual selection mask are, in this example, essentially strips which extend perpendicularly to the general orientation of the facets of the girdle 18 and of the top 58 and bottom 60 edges of the girdle 18 where there girdle 18 meets respectively the crown 14 and the pavilion 16. Therefore, in this example, each selected zone of the master image comprises only two identification points IP01, IP02, IP11, IP12, . . . , IPi1, IPi2, . . . IPij, . . . . The location of each of these identification points, which each correspond to a detected facet edge portion image, may be stored electronically in a database record.

Figure 8:
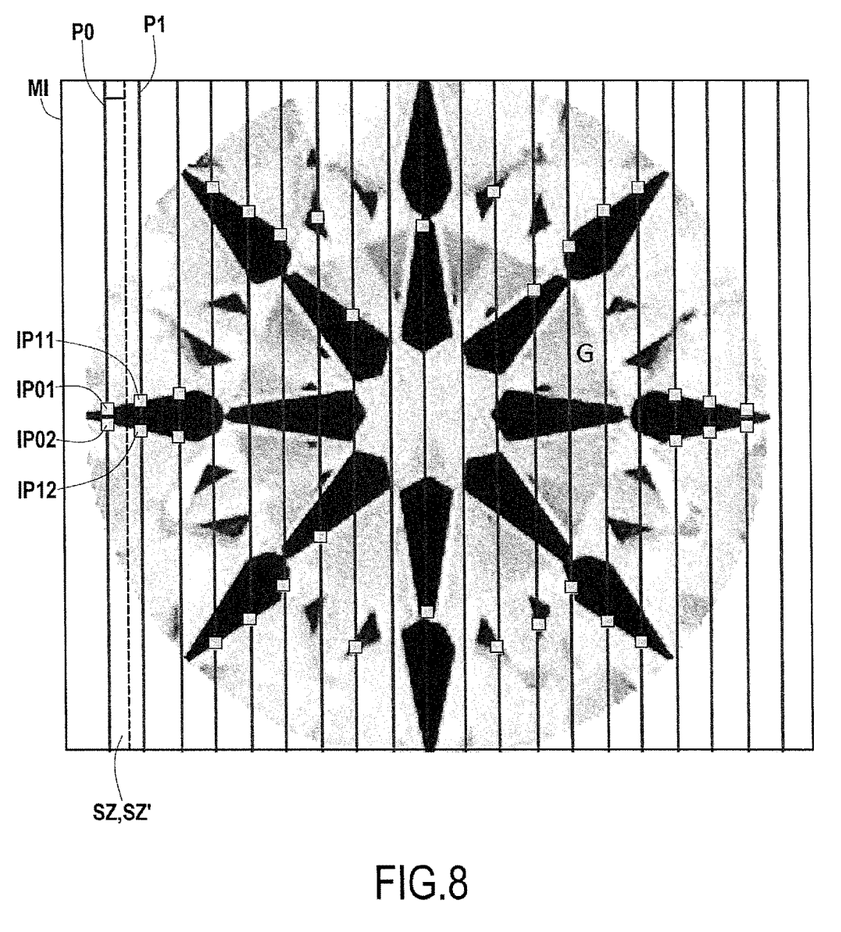
FIG. 8 illustrates the detection of facet edge portion images with a master image.
Figure 9:
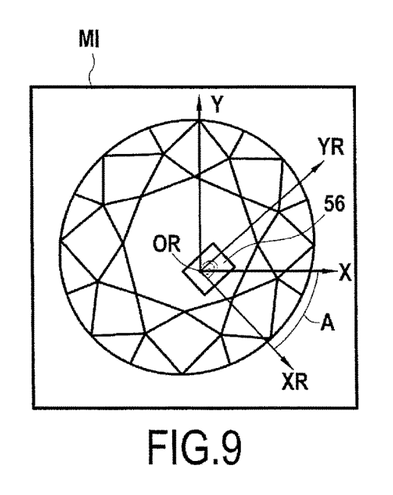
FIGS. 9 and 10 show a master image and its matching with a virtual selection mask for a different master image of the same zone of interest on the same gemstone as that of FIGS. 6 and 7, albeit with a different orientation of the gemstone during the acquisition of the master image.

In the example of FIG. 8, it is shown the case where, in some selected zones of the master image, more than two identification points could be determined, corresponding to more than two detected facet edge portion images in a given selected zone of the master image.

However, it is possible to choose that not all of the identification points are retained. For example in the example shown on FIG. 8, only two of the identification points are retained for one given selected zone of the master image. However, in such case, the method provides for a way of selecting always the same two identification points, for a given gemstone, if the method is used several times for the same gemstone. For example, it can be chosen that, to detect a first identification point, the edge detection technique, for example such as described above, is ran starting from one extremity of the selected zone, corresponding to one extremity of the associated selection path curve until a first identification point corresponding to a first detected facet edge portion image is found. Then, to detect the second identification point in the same selected zone, the edge detection technique is ran starting from of the other extremity of the selected zone, corresponding to the other extremity of the associated selection path curve, i.e. in the reverse direction, until a second identification point corresponding to the second detected facet edge portion image is found. The other facet edge portion images in the given selected zone may be ignored.

Thus, as describes above, in some embodiments, the method can involve detecting, in each of the plurality of distinct selected zones of the master image, the presence or not of two distinct facet edge portion images. It has also been illustrated that, in the presence of two detected facet edge portion images in a same selected zones of the master image, it is possible to define a location of the detected facet edge portion images in the master image. In other words, in each of the plurality of distinct selected zones of the master image, the edge detection technique is applied and retrieves zero, one or two identification points, the locations of which can be defined as the location of zero, one or two distinct facet edge portion images.

In those selected zones for which two distinct facet edge portion images are detected, it is possible to compute an inter-edge distance DIE between the two defined locations of the two detected facet edge portion images of the same selected zone which is considered. In the example of FIG. 5, the selection zone SZ'i has two identification points IPi1, IPi2. The inter-edge distance for this selected zone SZ'i is thus the distance, for example the geometrical distance, between the two identification points.

This inter-edge distance DIEi can be computed in the master image referential. In this referential, the coordinates of two given identification points IPi1, IPi2, corresponding each to the defined location of one detected facet edge portion image, can be assigned the coordinates IPi1 (Ni1, Mi1) and IPi2 (Ni2, Mi2) which may be expressed in pixels. In such case, the inter-edge distance DIEi for that given pair of identification points in the same selected zone can be expressed by the formula valid for geometrical distance:

$$DIEi = \sqrt{(Ni2-Ni1)^2 + (Mi2-Mi1)^2}$$

The value of the inter-edge distance DIEi may be rounded up to its integer part, to have an integer number.

Thus for example, the unique identifier for a given gemstone can be computed using various inter-edge distances for a number of pair of identification points detected for that gemstone, especially for pair of identification points detected in the same selected zone of the master image.

Thus, the method according to the invention allows for determining, for a given gemstone, a unique set of values, for example the values DOij and/or DIEi, which are based on the locations of some identifications points of the gemstone. This unique set of values is unique to the particular gemstone. The unique set of values is retrieved via digital image acquisition and digital image analysis involving digital computation. The unique set of values is preferably an electronic record, which can be stored electronically, at least transiently.

The method has good repeatability, in that if the method is performed several times for a same gemstone, it will retrieve the same unique set of values DOij and DIEi, at least to the extent necessary for having the necessary discrimination between two gemstones. The unique set of values thus retrieved can it itself constitute a unique identifier of the gemstone. The unique identifier can be computed based on this unique set of values, using algorithms.

Preferably, the unique identifier will be computed by the computing system, for example the computer 28. The unique identifier can be computed into a sequence of bits, which may represent an alphanumeric string, so that it can be electronically stored on a digital data storage device or transmitted across a communications link. As an example, the unique identifier can be composed or can comprise a concatenation of the unique set of values, for example the values DOij and DIEi, which are based on the locations of some identifications points of the gemstone.

The unique identifier may be secure or non-secure. That is to say, the unique identifier may or may not be protected with a cryptographic mechanism, such as, but not limited to, encryption and/or digital signature.

The unique identifier, if it is computed for the first time for a given gemstone, is then preferably electronically stored under a digital form in an electronic database, for example an original identifiers database, which may be hosted on a digital data memory device pertaining to the computer system. In said database, the unique identifier may be associated with other information relating to the corresponding gemstone. If the method is performed a subsequent time after an initial computation relating to a given gemstone, the retrieved unique identifier can be compared to the original identifiers in the original identifiers database to find a matching original identifier. If a matching original identifier is found, then the gemstone is positively identified and the associated items of information for that gemstone can be retrieved.

In the example, the unique identifier can be computed based on the computed origin distances and on the computed inter-edge distances for the detected facet edge portion images.

The systems and methods described herein can be implemented in software or hardware or any combination thereof. The systems and methods described herein can be implemented with a computing device such as computer 28 or using one or more computing devices, which may or may not be physically or logically separate from each other. Additionally, various aspects of the methods described herein may be combined or merged into other functions. In some embodiments, the illustrated system elements could be combined into a single hardware device or separated into multiple hardware devices. If multiple hardware devices are used, the hardware devices could be physically located proximate to or remotely from each other.

The methods can be implemented in a computer program product accessible from a computer-usable or computer-readable storage medium that provides program code for use by or in connection with a computer or any instruction execution system such as a computing device. A computer-usable or computer-readable storage medium can be any apparatus that can contain or store the program for use by or in connection with the computer or instruction execution system, apparatus, or device.

A computing device suitable for storing and/or executing the corresponding program code can include at least one processor coupled directly or indirectly to digital data storage devices such as memory elements. Input/output (I/O) devices (including but not limited to keyboards, displays, pointing devices, etc.) can be coupled to the computing device. Network adapters may also be coupled to the system to enable the computing device to become coupled to other computing devices or remote printers or storage devices through intervening private or public networks. To provide for interaction with a user, the features can be implemented on a computer with a display device, such as a CRT (cathode ray tube), LCD (liquid crystal display), or another type of monitor for displaying information to the user, and a keyboard and an input device, such as a mouse or trackball by which the user can provide input to the computer.

A computer program can be a set of instructions that can be used, directly or indirectly, in a computing device such as a computer. The systems and methods described herein can be implemented using programming languages such as Flash™, JAVA™, C++, C, C#, Visual Basic™, JavaScript™, PHP, XML, HTML, etc., or a combination of programming languages, including compiled or interpreted languages, and can be deployed in any form, including as a stand-alone program or as a module, component, subroutine, or other unit suitable for use in a computing environment. The software can include, but is not limited to, firmware, resident software, microcode, etc. Protocols such as SOAP/HTTP may be used in implementing interfaces between programming modules. The components and functionality described herein may be implemented on any desktop operating system executing in a virtualized or non-virtualized environment, using any programming language suitable for software development, including, but not limited to, different versions of Microsoft Windows™, Apple™ Mac™, iOS™, Unix™/X-Windows™, Linux™, etc.

Suitable processors for the execution of a program of instructions include, but are not limited to, general and special purpose microprocessors, and the sole processor or one of multiple processors or cores, of any kind of computer. A processor may receive and store instructions and data from a digital data storage device such as a read-only memory, a random access memory, both, or any combination of the data storage devices described herein. A processor may include any processing circuitry or control circuitry operative to control the operations and performance of an electronic device.

The processor may also include, or be operatively coupled to communicate with, one or more digital data storage devices for storing data. Such digital data storage devices can include, as non-limiting examples, magnetic disks (including internal hard disks and removable disks), magneto-optical disks, optical disks, read-only memory, random access memory, and/or flash storage. Digital Storage devices suitable for tangibly embodying computer program instructions and data can also include all forms of non-volatile memory, including, for example, semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The systems and methods described herein can be implemented using any combination of software or hardware elements. The systems and methods described herein can be implemented using one or more virtual machines operating alone or in combination with each other. Any applicable virtualization solution can be used for encapsulating a physical computing machine platform into a virtual machine that is executed under the control of virtualization software running on a hardware computing platform or host. The virtual machine can have both virtual system hardware and guest operating system software.

The systems and methods described herein can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include, for example, a LAN, a WAN, and the computers and networks that form the Internet.

One or more embodiments of the invention may be practiced with other computer system configurations, including hand-held devices, microprocessor systems, microprocessor-based or programmable consumer electronics, minicomputers, mainframe computers, etc. The invention may also be practiced in distributed computing environments where tasks are performed by remote processing devices that are linked through a network.

The invention claimed is:

1. A method for computing a unique identifier for a gemstone having facets separated by facet edges, comprising:
    acquiring a 2D digital master image of the gemstone with a digital photographic imaging device, the digital image comprising a 2D array of pixels having a pixel value, where an image of a reference mark on the gemstone is included in the master image at a reference location with a reference orientation, thus defining a master image referential based on the reference location and on the reference orientation;
    using a predefined virtual selection mask wherein the virtual selection mask comprises a series of distinct selection zones, and matching the virtual selection mask with the master image according to a predefined virtual selection mask position and predefined virtual selection mask orientation with respect to the master image referential;
    defining, in the master image, a plurality of distinct selected zones corresponding to the location of the selection zones of the matched mask;
    detecting, in each of the plurality of distinct selected zones of the master image, the presence or not of at least one facet edge portion image;
    in the presence of at least one detected facet edge portion image, defining a location of the detected facet edge portion images in the master image;
    computing a unique identifier based on the defined locations of the detected facet edge portion images.

2. A method according to claim 1, wherein the unique identifier is computed based on a computed origin distance for the detected facet edge portion images, where the origin distance for a detected facet edge portion image is the distance between the defined location of the detected facet edge portion image and the reference location of the reference mark.

3. A method according to claim 2, comprising:
    detecting, in each of the plurality of distinct selected zones of the master image, the presence or not of two distinct facet edge portion images;
    in the presence of two detected facet edge portion images in a same selected zone of the master image, defining a location of each of the two detected facet edge portion images in the master image and computing an inter-edge distance between the two defined locations of the detected facet edge portion images;
    computing the unique identifier based on the computed inter-edge distances.

4. A method according to claim 3, wherein the unique identifier is computed based on the computed origin distances and on the computed inter-edge distances for the detected facet edge portion images.

5. A method according to claim 1, wherein a selection zone of the virtual selection mask is defined by a selection path curve associated with an analysis window having an analysis area measured in pixels, a selected zone in the master image being the array of pixels of the master image which are covered by the analysis window when the analysis window of a corresponding selection zone of the matched virtual selection mask is circulated along the associated selection path curve.

6. A method according to claim 5, wherein the series of selection zones of the virtual selection mask is defined by at least one series of distinct selection path curves.

7. A method according to claim 5, wherein the series of selection zones of the virtual selection mask is defined by at least one series of distinct parallel selection path curves.

8. A method according to claim 5, wherein the series of selection zones of the virtual selection mask is defined by at least one series of distinct parallel straight selection path lines.

9. A method, wherein a facet edge portion image is detected by:
- computing a window value for successive window positions of the analysis window along the selection path curve of a selection zone, where the window value for a given window position along the selection path curve is computed based on the pixel values of pixels of the master image which are covered by the analysis window at said given position;
- monitoring the variation of the window value when the analysis window is circulated along the selection path curve;
- detecting a facet edge portion image based on the variation of the window value.

10. A method according to claim 9, wherein a facet edge portion image is detected when the variation of the window value shifts with respect to a threshold value.

11. A method according to claim 1, wherein the method includes a prior step of placing the gemstone with respect to the imaging device in a position and orientation so that the image of the reference mark on the gemstone is included in the master image at a predefined reference position.

12. A method according to claim 1, wherein the method includes a prior step of placing the gemstone with respect to the imaging device in a position and orientation so that the image of the reference mark on the gemstone is included in the master image with a predefined orientation.

13. A method according to claim 1, wherein the reference mark is a preexisting known reference mark on the gemstone.

14. A method according to claim 1, wherein the master image is acquired under specified illumination conditions.

15. A method according to claim 1, comprising:
- detecting, in each of the plurality of distinct selected zones of the master image, the presence or not of two distinct facet edge portion images;
- in the presence of two detected facet edge portion images in a same selected zone of the master image, defining a location of each of the two detected facet edge portion images in the master image and computing an inter-edge distance between the two defined locations of the detected facet edge portion images;
- computing the unique identifier based on the computed inter-edge distances.

* * * * *

UNITED STATES PATENT AND TRADEMARK OFFICE
CERTIFICATE OF CORRECTION

PATENT NO. : 10,489,647 B2
APPLICATION NO. : 15/950278
DATED : November 26, 2019
INVENTOR(S) : Nicolas Schaefer

Page 1 of 1

It is certified that error appears in the above-identified patent and that said Letters Patent is hereby corrected as shown below:

On the Title Page

Foreign Application Priority Data should be noted as follows:
Apr. 14, 2017 (EP) 17166692.8

Signed and Sealed this
Seventeenth Day of March, 2020

Andrei Iancu
*Director of the United States Patent and Trademark Office*